United States Patent [19]

Clendenin

[11] 4,312,212
[45] Jan. 26, 1982

[54] APPARATUS FOR TESTING THE TACK TIME OF EPOXY PREPREG

[75] Inventor: William H. Clendenin, Coshocton, Ohio

[73] Assignee: General Electric Company, Coshocton, Ohio

[21] Appl. No.: 140,736

[22] Filed: Apr. 16, 1980

[51] Int. Cl.³ ............................................. G01N 33/34
[52] U.S. Cl. .................................... 73/15.4; 73/17 R; 73/150 R
[58] Field of Search ........................ 73/15.4, 17 R, 150

[56] References Cited

U.S. PATENT DOCUMENTS

| | | | |
|---|---|---|---|
| 2,038,622 | 4/1936 | Yeager | 73/15.4 |
| 2,574,715 | 11/1951 | Sontag | 73/15.4 |
| 2,775,888 | 1/1957 | Pickup | 73/150 |
| 3,368,398 | 2/1968 | Skewis | 73/150 |

*Primary Examiner*—S. Clement Swisher
*Attorney, Agent, or Firm*—Morgan, Finnegan, Pine, Foley & Lee

[57] ABSTRACT

An apparatus is disclosed to simplify the measurement of tack time which is the length of time necessary to heat the prepreg to a tacky condition. A strip of a prepreg specimen is wrapped around an elongated lower support member, and thereafter an upper support member is fixedly connected to the lower support member to secure the prepreg in place. The thickness of the coiled prepreg causes the upper support member to flex upwardly in a bow-like configuration defining a pair of channels between the support members on either side of the coiled prepreg. A head member, having a planar bottom surface, includes a pair of gripping members which are received in the channels between the support members for gripping the prepreg specimen. An electrically controlled air cylinder is provided having a reciprocating piston which is connected to the head member for sequentially moving the prepreg specimen into and out of contact with a heated platen. In use, the prepreg specimen is heated while it is pressed into contact with the platen by the head member, thereby causing the epoxy resin contained therein to melt. The repeated lifting of the prepreg by the reciprocating piston, out of contact with the platen, enables any occurrence of stringiness or tackiness to be observed. An elapsed time counter is provided which measures the interval from the initiation of the test until stringing occurs which corresponds to the tack time of the specimen.

11 Claims, 4 Drawing Figures

APPARATUS FOR TESTING THE TACK TIME OF EPOXY PREPREG

BACKGROUND OF THE INVENTION

An apparatus for testing the tack time of an epoxy prepreg glass cloth strip is provided which enables the simple and automatic measurement of the tack time of a prepreg sample. The apparatus enables the tack time test to be uniformly repeated with various samples and provides controlled pressures and constant timing sequences.

The tack time test is a quantitative measurement which relates to the degree of cure of epoxy impregnated fiberglass cloth. Epoxy prepregs such as bonding sheets and multilayer laminates are utilized for example, in the fabrication of printed circuit boards. In order to provide a standard reference for comparing the amount of partial curing of various prepregs, the United States Military developed a "tack time test" procedure which is used by manufacturers to classify their product. The tack time test as recited in Mil G-55636A at 4.6.8, requires that a strip of epoxy prepreg of approximately one inch in width and ten inches in length be wrapped around one end of a tongue depressor adjacent its distal end. A second tongue depressor is employed to secure the free end of the prepreg by positioning it directly over the first tongue depressor and fastening the two tongue depressors together at their middle. The prepreg is then placed firmly against a steel platen which is heated to 171°±1.5° C., while simultaneously initiating a timing sequence. At ten second intervals, the specimen of the prepreg is lifted from the heated platen for one second and the resin is observed to determine the presence of tackiness. As the epoxy resin approaches the gel point, it becomes increasingly tacky until it begins to string. The "tack time" is a measurement of the length of interval starting from the initiation of the test until distinct and continuous stringing occurs between the prepreg and the heated platen when the prepreg specimen is lifted off the platen.

The methods and assemblies for conducting the above described tack time test, which was established to provide uniformity throughout the field, suffered from certain shortcomings. More specifically, makeshift attempts to repeatedly carry out the above described test often failed to achieve the uniformity necessary to enable purchasers to rely on the results. Stated differently, absent an assembly to carry out the tack time test, many variables are often introduced into the procedure which affect the consistency of the results. For example, the tack time of a particular specimen will vary if the amount of pressure which is applied to the prepreg while it is against the heated platen is varied. In addition, if there is deviation in the distance to which the prepreg is withdrawn from the platen, or in the amount of time the prepreg is separated from the heated platen, the point when stringing will first be observed will differ. Further, as can be appreciated, it is relatively difficult for an operator to move the prepreg into and out of contact with the platen and observe the prepreg for tackiness while simultaneously keeping track of specific time intervals and total elapsed time. Therefore, it would be desirable to provide an assembly which simplifies the testing of tack time and which can be used in aiding the standardization of the industry.

Accordingly, it is an object of the subject invention to provide a new and improved assembly for testing the tack time of epoxy prepreg glass cloth strips which sequentially moves a prepreg specimen into and out of contact with a heated platen while simultaneously keeping a record of elapsed time until continuous stringing is observed.

It is a further object of the subject invention to provide a new and improved assembly for testing the tack time of epoxy prepreg which can consistently operate with fixed time intervals and produce uniform pressures to enable the accurate reproduction of test data.

It is another object of the subject invention to provide an assembly for testing the tack time of epoxy prepreg wherein the distance which the prepreg is lifted away from the platen, during testing, is accurately controlled.

SUMMARY OF THE INVENTION

In accordance with these and many other objects, the subject invention provides a tack time testing assembly which includes an improved prepreg mounting means. More specifically, the prepreg mounting means consists of a pair of opposed elongated support members such as tongue depressors, as used heretofore. A prepreg specimen strip is wrapped around the central area of the lower support member and thereafter the upper support member is affixed to the lower support member, at their distal ends, thereby securing the coiled prepreg in place. The thickness of the coiled specimen causes the upper member to flex upwardly into a bow-like configuration thereby providing a pair of channels between the support members on either side of the coiled prepreg.

The prepreg mounting means is intended to be mounted on the new and improved tack time testing apparatus. The tack time testing apparatus includes an air cylinder having a reciprocating piston, which will sequentially raise and lower the prepreg speciment into and out of contact with a heated platen. More particularly, the piston of the air cylinder is connected to a novel head member having a planar bottom surface and including a gripping means connected thereto. The gripping means of the subject invention includes a pair of spaced tine members which are disposed below and spaced from the plane of the bottom surface of the head member. The prepreg mounting means may be readily installed on the head member with the tine members being receivable in the channels formed in the mounting means.

At the initiation of the tack time test, the piston of the air cylinder will force the head member downwardly until the planar bottom surface thereof presses the prepreg into abutting relationship with the heated platen. In a preferred embodiment, an air pressure regulator is provided in the supply line of the air cylinder for maintaining a constant, repeatable downward force on the specimen. In accordance with standard operating procedures, at ten second intervals, the air cylinder raises the head member and the specimen to enable the operator to observe any occurrence of tackiness. The piston of the air cylinder continues to sequentially reciprocate in a timed sequence until the operator observes a distinct and continuous stringing between the prepreg specimen and the platen. At this point an elapsed time counter associated with the apparatus discloses the tack time of the specimen. In a preferred embodiment of the subject invention, a means is provided to control the distance which the specimen is raised from the platen.

Further objects and advantages of the subject invention will become apparent from the following detailed description taken in conjunction with the drawings in which:

DESCRIPTION OF THE PREFERRED EMBODIMENT

Figure 1:
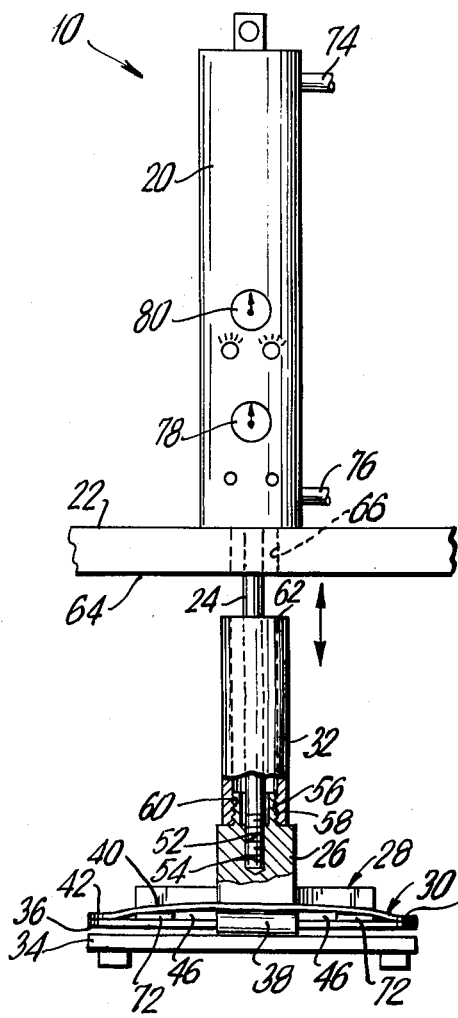
FIG. 1 is an elevational view of the tack time tester assembly of the subject invention.

Referring generally to FIG. 1, the assembly 10 for testing the tack time of an epoxy prepreg glass cloth specimen is illustrated and includes an air cylinder 20 mounted on a support platform 22 and having a reciprocating piston 24. The piston 24 is connected to a head member 26 which includes a gripping means 28 for holding the prepreg mounting means 30. A sleeve 32 is mounted on the head member 26 for controlling the distance which the prepreg is lifted off the platen 34.

Figure 2:
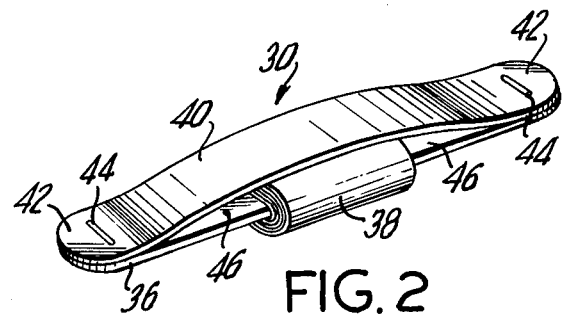
FIG. 2 is a perspective view of the prepreg mounting means of the subject invention.

Referring more specifically to FIG. 2, an enlarged view of the improved prepreg mounting means 30 of the subject invention is illustrated. More specifically, the prepreg mounting means 30 includes a lower support member 36 which may for example be a wooden tongue depressor, as used heretofore in the prior art. A strip of the epoxy impregnated fiberglass cloth specimen, which is approximately one inch wide and ten inches long, is wrapped around the central portion of the lower support member 36 forming a coil 38. An upper support member 40 which may also be a tongue depressor, is utilized to hold the coiled prepreg specimen 38 in place. More particularly, after support member 40 is pressed into contact with the coiled prepreg specimen 38, the distal ends 42 of the support members 36, 40 are fixedly connected, by staples 44 or other suitable means. As is apparent from FIG. 2, the thickness of the coiled prepreg 38 causes the upper support member 40 to flex upwardly in a bow-like configuration thereby defining a pair of channels 46 disposed between the support members 36 and 40 and adjacent the opposed sides of the coiled prepreg 38. Tine members 72 of the gripping means 28 are receivable in channels 46 of the prepreg mounting means 30 thereby providing a simple method of securing the mounting means to the head member 26 as more fully described hereinafter.

Figure 3:
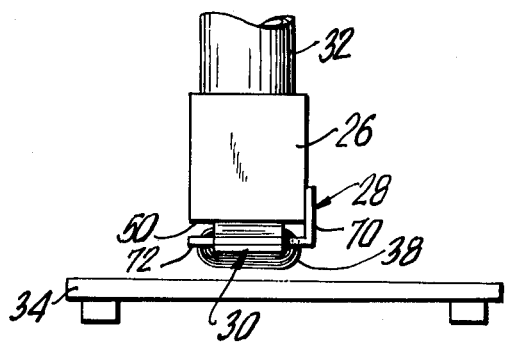
FIG. 3 is a side elevational view of the head member of the subject invention in a raised position.
Figure 4:
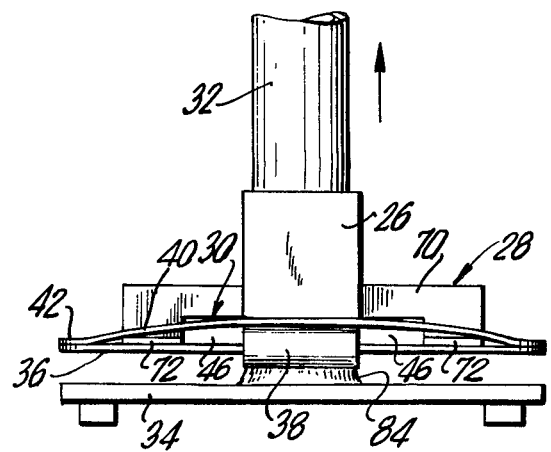
FIG. 4 is a front elevational view of the head member of the subject invention in a raised position illustrating the distinct and continuous stringing between the specimen and the heated platen.

Referring now more specifically to FIGS. 3 and 4, the new and improved head member 26 of the subject invention is illustrated and is formed from a generally rectangular aluminum block having a planar bottom surface 50 for exerting downward pressure on the prepreg specimen 38 through upper support member 40. The head member 26 is connected to the piston 24 in any suitable manner. For example, head member may be provided with a threaded aperture 52 for receiving the threaded lower end 54 of the piston 24. The upper end of the head member 26 is provided with an upwardly extending cylindrical extension 56 having threads 58 on the outer surface thereof. The inner surface of the lower end of sleeve 32 is provided with matching threads 60 such that by rotating the sleeve 32 about its central axis its position, relative to the upper surface of head member 26 will be varied, and more importantly, the distance between the upper end 62 of the sleeve 32 and the lower surface 64 of the support platform 22 will be varied. By this arrangement, the height which the prepreg specimen 38 is lifted off the platen 34 by the piston 24 may be accurately controlled. More specifically, during the upward stroke of the piston 24, the prepreg specimen 38 will be raised until the movement of the piston is arrested when the upper end 62 of the sleeve 32 comes into abutting contact with the lower surface 64 of the support platform 22. Thus, the sleeve 32 prevents the piston 24 from retracting any further into the air cylinder 20 thereby controlling the maximum height to which the prepreg is lifted off the platen 34. As is apparent, by rotating the sleeve 32, the distance between the upper surface 62 thereof and the lower surface 64 of the support platform 22 is varied. It is intended that once the tack time test operation has begun, this distance is not varied such that the prepreg specimen 38 is repeatedly lifted to the same height. The planar support platform 22, upon which the air cylinder is mounted preferably includes a circular aperture 66 therein to enable the free movement of the piston 24. The diameter of the circular aperture 66 is less than the diameter of the sleeve 32 such that when the piston 24 moves upwardly, the upper surface 62 thereof will come into abutting contact with the lower surface 64 of the support platform 22.

Head member 26 is further provided with an improved gripping means 28 which includes a planar vertical cross bar member 70 and a pair of spaced horizontally extending planar tine members 72. The cross bar 70 is affixed directly to the rear of the head member 28 such that the tine members 72 are disposed below and spaced from the planar bottom surface 50 of the head member 26.

The gripping means 28 facilitates the rapid mounting of the prepreg mounting means 30 onto the head member 26. More specifically, the horizontally extending tine members 72 are readily receivable in the channels 46 of the mounting means 30. By this arrangement, and as illustrated in FIGS. 1 and 4, when the piston 24 raises the head member 28, the tine members 72 draw the prepreg mounting means 30 upwardly, away from the platen 34, to enable the operator to observe any stringing occurring between the specimen 38 and the platen 34. In contrast, when the piston 24 is in the downward position, pressure from the underside 50 of the head member 28 is transmitted to the prepreg specimen 30 via the upper support member 40.

The remainder of the control mechanisms for the subject assembly 10 are associated with the air cylinder 20. More specifically, compressed air is delivered to the air cylinder 20 via tubes 74 and 76 and is alternately channeled thereto by a solenoid valve (not shown). The solenoid valve is controlled by an electrical timing device 78. It is noted that for purposes of clarity, the timing devices are shown attached directly to the air cylinder 20, however, the scope of the subject invention is intended to include any arrangement wherein the timing mechanisms are operatively associated with the air cylinder. The timing device 78 is set to cause the piston to reciprocate in accordance with standard procedures. Preferably the timing device 78 includes an elapsed time counter which registers the length of the test procedure, from the initiation thereof until continuous stringing is observed between the prepreg specimen 38 and the heated platen 34. The pressure which the head member 26 exerts on the prepreg specimen 38 is controlled by an air pressure regulator 80. Preferably the air pressure regulator 80 is set to provide a maximum pressure of approximately three pounds per square inch.

In operation, initially platen 34 is heated to a temperature of 171°±1.5° C. The prepreg mounting means 30 is set up with the particular specimen to be tested in the manner previously described, with the prepreg strip 38 being wound around the lower support member 36 and with the upper support member 40 being secured thereto at its distal ends 42, as illustrated in FIG. 2. The mounting means 30 is then mounted on the head member 28 with the tine members 72 being received in the channels 46 of the mounting means 30. Thereafter, the standard timing sequence is begun, which causes the piston 24 to move downwardly such that the bottom surface 50 of the head member 26 presses the prepreg specimen 38 onto the upper surface of the heated platen 34. As noted above, the air pressure regulator 80 is set such that a constant uniform pressure is maintained against the specimen 38 which is preferably approximately three pounds per square inch.

After the chosen time interval has elapsed, the electrically controlled timing device 78 causes the piston 24 to begin its upward stroke, with the gripping means 28 of the head member 26 lifting the prepreg specimen 38 out of contact with the heated platen 34. The piston 24 continues its upward stroke until the upper surface 62 of the sleeve 32 comes into abutting relationship with the lower surface 64 of the support member 22, thereby arresting the piston stroke. At this time, and as illustrated in FIG. 3, the operator can observe if any tackiness or stringing has occurred between the specimen 38 and the platen 34. If no stringing is observed, the timing device 78 will continue to cause the piston 24 to reciprocate in accordance with the test procedure, thereby alternatively pressing the specimen 38 into contact with the heated platen 34, and thereafter lifting the specimen away from the platen 34. This sequence is repeated until, as illustrated in FIG. 4, the operator observes distinct and continuous stringing 84 between the prepreg specimen 38 and the heated platen 34. At this point the apparatus 10 is shut off with the elapsed time counter registering the length of time since the initiation of the operation, which corresponds to the tack time of the specimen.

Accordingly, the subject invention provides for an assembly which simplifies the tack time testing procedure. Further, the subject assembly allows the test to be run under uniform repeatable conditions such that industry wide standardization is facilitated.

In summary, the subject tack time testing assembly includes a prepreg mounting means 30 which includes upper and lower opposed elongated support members 36, 40 which are fixedly connected at their distal ends. A strip of prepreg specimen 38 is wrapped around the lower support member with the thickness thereof causing the upper support member to be flexed upwardly in a bow-like configuration to define a pair of open channels 46 between the support members and on either side of the coiled prepreg strip. A head member 26 is provided having a planar bottom surface 50 and including a means 28 for gripping the prepreg mounting means. An air cylinder 20 with a reciprocating piston 24 is provided for sequentially raising and lowering the head member 26 such that the prepreg mounting means 30 and the prepreg strip 38 are brought into and out of contact with a heated platen 34. By this arrangement, when the prepreg strip is pressed into contact with the platen by the head member, the epoxy therein will begin to melt. The repeated raising of the prepreg strip out of abutting contact with the heated platen by the air cylinder enables any occurrence of stringing of the epoxy between the prepreg strip and the platen to be observed. In the preferred embodiment, an elapsed time counter is provided which measures the time between initiation of the operation and the occurrence of stringing which corresponds to the tack time of the specimen.

Although the subject assembly has been described by reference to a preferred embodiment, it is apparent that other modifications could be devised by those skilled in the art that would fall within the scope and spirit of the subject invention as defined by the appended claims.

What is claimed is:

1. An assembly for testing the tack time of an epoxy prepreg glass cloth strip, said assembly comprising:

prepreg mounting means, including upper and lower opposed elongated support members, said support members being fixedly connected at their distal ends, with said prepreg strip being wrapped around said lower support member at a point intermediate the distal ends thereof, such that the thickness of said coiled prepreg strip causes said upper support member to be flexed upwardly in a bow-like configuration thereby defining a pair of open channels between said support members and disposed adjacent the opposed sides of said coiled prepreg strip;

a head member having a planar bottom surface, said head member further including a gripping means connected to said head member for holding said prepreg mounting means, said gripping means including a pair of spaced tine members disposed below and spaced from the plane of said bottom surface of said head member, said tine members being receivable in said open channels in said mounting means thereby gripping said mounting means;

a planar heated platen disposed below said head member; and reciprocating means operatively associated with said head member for sequentially raising and lowering said head member such that said prepreg mounting means and coiled prepreg strip are brought into and out of abutting contact with said heated platen whereby during the operation of said apparatus, said prepreg strip is heated while pressed into contact with said platen by said head member thereby causing the epoxy therein to melt and wherein the repeated raising of said prepreg strip out of abutting contact with said heated platen by said reciprocating means enables any occurrence of the stringing of the epoxy, between said prepreg strip and said platen, to be observed, with the time elapsing between the initiation of said operation and the occurrence of said stringing corresponding to the tack time of the prepreg strip.

2. An assembly for testing the tack time of a prepreg strip as recited in claim 1 further including a means operatively associated with said assembly, for measuring the time interval from the initiation of said tack time test until stringing is observed between said prepreg strip and said platen which corresponds to the tack time of said prepreg strip.

3. An assembly for testing the tack time of a prepreg strip as recited in claim 1 further including a means for controlling the sequential raising and lowering of said reciprocating means.

4. An assembly for testing the tack time of a prepreg strip as recited in claim 1 wherein the distal ends of said support members are fixedly connected by staples.

5. An assembly for testing the tack time of a prepreg strip as recited in claim 1 wherein said reciprocating means comprises an air cylinder having a downwardly extending reciprocating piston, said piston being connected to said head member, and with said air cylinder being mounted on a planar support platform which is disposed in spaced parallel relationship to said planar heated platen.

6. An assembly for testing the tack time of a prepreg strip as recited in claim 5 further including a means for controlling the distance to which said head member is raised from said heated platen during the testing operation.

7. An assembly for testing the tack time of a prepreg strip as recited in claim 6 wherein said control means includes a hollow cylindrical sleeve surrounding said piston and extending upwardly from said head member, said sleeve being adjustably connected to said head member such that the position of the upper surface of said sleeve relative to the lower surface of said planar support platform may be varied.

8. An assembly for testing the tack time of a prepreg strip as recited in claim 7 wherein said support platform is provided with a circular aperture aligned coaxially with said piston thereby enabling said piston to reciprocate freely therein, and wherein the diameter of said circular aperture is less than the diameter of said sleeve whereby when said piston is raised, the upper surface of said sleeve abuts the lower surface of said support platform thereby halting the upward movement of said piston and determining the maximum height to which the prepreg strip is raised from said heated platen.

9. An assembly for testing the tack time of a prepreg strip as recited in claim 8 wherein said head member further includes a cylindrical extension, extending upwardly from the upper surface thereof, said extension being threaded on the outer surface thereof, and with the lower end of said sleeve being provided with threads on the inner surface thereof for engagement with said threads of said cylindrical extension of said head member, whereby the rotation of said sleeve functions to vary the position of said sleeve relative to said head member and the lower surface of said planar support platform.

10. An assembly for testing the tack time of a prepreg strip as recited in claim 5 further including an air pressure regulator connected to said air cylinder such that the force exerted on said prepreg strip when said strip is pressed into contact with said heated platen by said head member may be accurately controlled.

11. An assembly for testing the tack time of a prepreg strip as recited in claim 3 wherein said means for controlling the sequential raising and lowering of said reciprocating means further includes a means for timing each cycle, whereby if no stringing is observed, said timing means will continue to cause the reciprocating means to alternatively press the specimen into contact with said heated platen and thereafter lift the specimen away from the platen, until distinct and continuous stringing is observed.

* * * * *